United States Patent
Goedeke et al.

(10) Patent No.: US 6,687,547 B2
(45) Date of Patent: Feb. 3, 2004

(54) METHOD AND APPARATUS FOR COMMUNICATING WITH AN IMPLANTABLE MEDICAL DEVICE WITH DTMF TONES

(75) Inventors: Steven D. Goedeke, Forest Lake, MN (US); Charles H. Dudding, Lino Lakes, MN (US)

(73) Assignee: Medtronic, Inc., Minneapolis, MN (US)

(*) Notice: Subject to any disclaimer, the term of this patent is extended or adjusted under 35 U.S.C. 154(b) by 365 days.

(21) Appl. No.: 09/812,096

(22) Filed: Mar. 19, 2001

(65) Prior Publication Data

US 2001/0012955 A1 Aug. 9, 2001

Related U.S. Application Data

(63) Continuation-in-part of application No. 09/395,925, filed on Sep. 14, 1999, now Pat. No. 6,263,246.

(51) Int. Cl.⁷ .................................................. A61N 1/08
(52) U.S. Cl. ......................... 607/60; 128/904; 607/32
(58) Field of Search .............................. 607/60, 30, 31, 607/32; 128/904

(56) References Cited

U.S. PATENT DOCUMENTS

| | | |
|---|---|---|
| 4,146,029 A | 3/1979 | Ellinwood, Jr. |
| 4,601,291 A | 7/1986 | Boute et al. |
| 4,692,147 A | 9/1987 | Duggan |
| 5,107,833 A | 4/1992 | Barsness |
| 5,113,869 A | 5/1992 | Nappolz et al. |
| 5,331,966 A | 7/1994 | Bennett et al. |
| H1347 H | 8/1994 | Greeninger et al. .......... 607/30 |
| 5,342,408 A | 8/1994 | DeCoriolis et al. |
| 5,342,409 A | 8/1994 | Mullett |
| 5,354,319 A | 10/1994 | Wyborney et al. |
| 5,372,607 A | 12/1994 | Stone et al. |
| 5,383,909 A | 1/1995 | Keimel |

(List continued on next page.)

Primary Examiner—Kennedy Schaetzle
(74) Attorney, Agent, or Firm—Girma Wolde-Michael; Daniel G. Chapik

(57) ABSTRACT

Uplink and downlink telemetry between an implantable medical device (IMD) telemetry transceiver and an external medical device (EMD) telemetry transceiver used by a patient or health care provider is facilitated by the communications system of the present invention. The IMD provides a therapy and/or measures physiologic conditions of the patient for use in formulating a therapy and/or for storage in IMD memory for later uplink telemetry transmission. The patient causes the EMD to emit encoded dual tone multiple frequency (DTMF) tones that are detected by an audio receiver of the IMD to enable uplink and downlink telemetry transmissions in a telemetry or communication session. Then, the patient formulates a message via a message entry mechanism of the EMD that communicates an instruction or query to the IMD. The downlink message is optionally displayed by an EMD display as it is composed by the user and is then downlink telemetered to the IMD. A responsive uplink message from the IMD is uplink telemetered, received by the EMD telemetry transceiver, stored in EMD memory and displayed by EMD display. The EMD optionally includes a DSVD/modem module for either connection to a telephone line or a cellular telephone receiver in a variety of ways that can provide two-way voice communication between the patient and a remote care provider as well as transmission of uplink telemetered IMD and patient data to a remote EMD. The IMD may further include an audio tone generator for generating a tone or series of tones indicative of operation or status of the IMD that can be heard by the patient or received and displayed by the IMD. The DTMF tones can also be employed to alter an IMD operation.

51 Claims, 3 Drawing Sheets

U.S. PATENT DOCUMENTS

| | | | |
|---|---|---|---|
| 5,433,736 A | * 7/1995 | Nilsson | 607/59 |
| 5,456,692 A | 10/1995 | Smith, Jr. et al. | |
| 5,467,773 A | * 11/1995 | Bergelson et al. | 600/522 |
| 5,662,689 A | 9/1997 | Elsberry et al. | |
| 5,693,076 A | 12/1997 | Kaemmerer | |
| 5,721,783 A | 2/1998 | Anderson | 381/68.6 |
| 5,752,976 A | 5/1998 | Duffin et al. | 607/32 |
| 5,752,977 A | 5/1998 | Grevious et al. | |
| 5,772,575 A | * 6/1998 | Lesinski et al. | 600/25 |
| 5,843,138 A | 12/1998 | Evers et al. | |
| 5,843,139 A | 12/1998 | Goedeke et al. | |
| 5,941,829 A | 8/1999 | Saltzstein et al. | 600/509 |
| 6,044,301 A | 3/2000 | Hartlaub et al. | 607/31 |
| 6,070,102 A | 5/2000 | Hartlaub et al. | 607/31 |
| 6,083,248 A | 7/2000 | Thompson | 607/30 |
| 6,167,312 A | 12/2000 | Goedeke | 607/60 |
| 6,169,925 B1 | 1/2001 | Villaseca et al. | 607/60 |
| 6,236,889 B1 | * 5/2001 | Soykan et al. | 607/30 |

* cited by examiner

METHOD AND APPARATUS FOR COMMUNICATING WITH AN IMPLANTABLE MEDICAL DEVICE WITH DTMF TONES

This application is a continuation-in-part of U.S. patent application Ser. No. 09/395,925 filed Sep. 14, 1999, for METHOD AND APPARATUS FOR COMMUNICATING WITH AN IMPLANTABLE MEDICAL DEVICE in the names of Steven H. Goedeke and Charles H. Dudding, Jr., now U.S. Pat. No. 6,263,246.

FIELD OF THE INVENTION

The present invention relates generally to the field of implantable (or implanted) medical devices, and more particularly to uplink and downlink telemetry between an implantable medical device (IMD) telemetry transceiver and an external medical device (EMD) telemetry transceiver.

BACKGROUND OF THE INVENTION

At present, a wide variety of IMDs are commercially released or proposed for clinical implantation that are programmable in a variety of operating modes and are interrogatable using RF telemetry transmissions between the IMD and an externally located EMD. The terms "telemeter", "telemetry transmission" and the like are intended to embrace any action and manner of communicating and conveying patient data and downlink telemetry data between the IMD and any type of EMD in the uplink and downlink telemetry directions.

Typically, certain therapy delivery and monitoring operational modes and parameters of the IMD are altered temporarily or chronically in a non-invasive (i.e. non-surgical) manner using downlink telemetry transmission from an EMD of programming and interrogation commands or downlink messages herein also referred to as "downlink telemetry data". Moreover, a wide variety of real time and stored physiologic data as well as non-physiologic, IMD related, data or previously stored implant data (referred to collectively herein as "patient data") composed into uplink messages and are uplink telemetered by the IMD to the EMD in response to a downlink telemetered interrogation command that is received by the IMD transceiver.

The EMD is typically characterized as a full function or limited function "programmer". The full function programmers are implemented with a full range of programming and interrogation capabilities and are intended for use by a physician or other health care provider to communicate with the EMD. In certain instances, patients are provided with limited function programmers that typically have a limited range of programming functions and are intended for use by the patient to downlink telemeter a command to the IMD to deliver a therapy or change a therapy and/or to store physiologic data when the patient experiences particular symptoms.

A wide variety of IMDs have been developed for use in the human body to monitor the patient's condition and/or to treat a patients underlying disease state. Such IMDs include implantable cardiac pacemakers, cardioverter/defibrillators, cardiomyostimulators, pacemaker/cardioverter/defibrillators, drug delivery systems, cardiac and other physiologic monitors, electrical stimulators including nerve and muscle stimulators, deep brain stimulators, cochlear implants, and heart assist IMDs or pumps, etc.

Most of these IMDs are used in conjunction with the above-described EMDs that control the operation of the IMDs and receive information from the IMDs. Examples of programmable implantable pacemakers include U.S. Pat. No. 5,456,692, issued to Smith et al., U.S. Pat. No. 5,843,138, issued to Evers, U.S. Pat. No. 5,372,607, issued to Stone et al., U.S. Pat. No. 5,843,139, issued to Goedeke et al., U.S. Pat. No. 4,601,291, issued to Boute et al., U.S. Pat. No. 5,693,076, issued to Kaemmerer, et al., U.S. Pat. No. 5,752,977, issued to Grevious et al., U.S. Pat. No. 5,354,319 issued to Wyborny et al. and U.S. Pat. No. 5,107,833, issued to Barsness et al. Examples of the various other types of programmable IMDs listed above include U.S. Pat. No. 5,342,408, issued to DeCoriolis et al., U.S. Pat. No. 5,383,909, issued to Keimel, U.S. Pat. No. 4,146,029, issued to Ellinwood, U.S. Pat. No. 4,692,147, issued to Duggan, U.S. Pat. No. 5,662,689, issued to Ellsberry et al, U.S. Pat. No. 5,342,409, issued to Mullett, and U.S. Pat. No. 5,331,966, issued to Bennett et al.

In many of the systems described above, activation of telemetry from the IMD to the associated EMD requires placement of a magnet in physical proximity to the IMD. The same type of magnet may also activate a temporary change in IMD operation. The best-known example of such an operational mode change is the initiation of asynchronous pacing operation in an implantable pacemaker, enabling the patient or the patient's physician to conveniently determine the present pacing rate. This type of magnetically triggered mode change is also useful in the context of trans-telephonic pacemaker monitoring, allowing the remote monitoring IMD to record a paced electrogram, if desired.

The requirement of magnetic activation of the IMD's telemetry function or mode change, while serving as a useful safety feature, does have some drawbacks. First, the magnets employed are typically relatively heavy, high strength magnets of a type not typically available other than from the IMD manufacturer, making them inconvenient and expensive to replace in the event they are lost or broken. This does not pose a problem in the context of programming or monitoring the IMD using a programmer which employs a programming head placed in proximity to the patient's body, as such programming heads typically include a built-in magnet, typically an permanent magnet. However, as programming systems which employ programming antennas which may be remote from the body are developed, for example as disclosed in U.S. Pat. No. 5,113,869, issued to Nappholz et al., U.S. Pat. No. 6,169,925, issued to Villaseca et al., and U.S. Pat. No. 6,167,312, issued to Goedeke, a magnet within the programmer is not workable. Second, placement of the magnet in proper orientation and location with regard to the IMD is sometimes difficult, making the process more cumbersome than might be desirable.

SUMMARY OF THE INVENTION

The present invention is directed toward providing a mechanism that provides the functions typically provided by an externally applied magnet and an associated magnetic switch and circuitry within the IMD that overcomes problems as described above and advantageously enables the expansion of functions of a patient programmer or EMD.

An IMD according to the present invention provides a therapy and/or measures physiologic conditions of the patient for use in formulating a therapy and/or for storage in IMD memory for later uplink telemetry transmission. The IMD is provided with an audio receiver such as a microphone and internal associated circuitry capable of demodulating dual tone multiple frequency (DTMF) tones of the type employed in modern touch-tone telephones and recognizing a defined sequence of such DTMF tones. In accordance with a further aspect of the invention, the DTMF tones are emitted by an EMD when the EMD is operated to do so by a user, typically the patient receiving the IMD or a health care provider attending the patient. The IMD responds to or is "unlocked" by a defined sequence of DTMF tones emitted by the EMD and initiates uplink telemetry transmission or changes an IMD operational mode as was previously accomplished by means of the applied magnetic field.

In one method of the present invention, the patient causes the EMD to emit encoded dual tone multiple frequency (DTMF) tones that are detected by an audio receiver of the IMD to enable uplink and downlink telemetry transmissions in a telemetry or communication session or to alter an IMD operation. When a communication session is started, the patient formulates a message via a message entry mechanism of the EMD that communicates an instruction or query to the IMD. The downlink message is optionally displayed by an EMD display as it is composed by the user and is then downlink telemetered to the IMD. A responsive uplink message from the IMD is uplink telemetered, received by the EMD telemetry transceiver, stored in EMD memory and displayed by EMD display.

The EMD optionally includes a DSVD/modem module for either connection to a telephone line or a cellular telephone receiver in a variety of ways that can provide two-way voice communication between the patient and a remote care provider as well as transmission of uplink telemetered IMD and patient data to a remote EMD.

The IMD may further include an audio tone generator for generating a tone or series of tones indicative of operation or status of the IMD that can be heard by the patient or received and displayed by the IMD. The DTMF tones can also be employed to alter an IMD operation.

This summary of the invention and the objects, advantages and features thereof have been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be appreciated as the same becomes better understood by reference to the following detailed description of the preferred embodiment of the invention when considered in connection with the accompanying drawings, in which like numbered reference numbers designate like parts throughout the figures thereof, and wherein.

DETAILED DESCRIPTION OF THE PREFERRED EMBODIMENTS OF THE INVENTION

The present invention can be implemented in any IMD having uplink and downlink telemetry capabilities. As the technology advances, IMDs become ever more complex in possible programmable operating modes, menus of available operating parameters, and capabilities of monitoring increasing varieties of physiologic conditions and electrical signals which place ever increasing demands on the telemetry transmission system. It is also contemplated that the present invention may be implemented in more than one IMD implanted within the same patient to enable communication between them.

Figure 1:
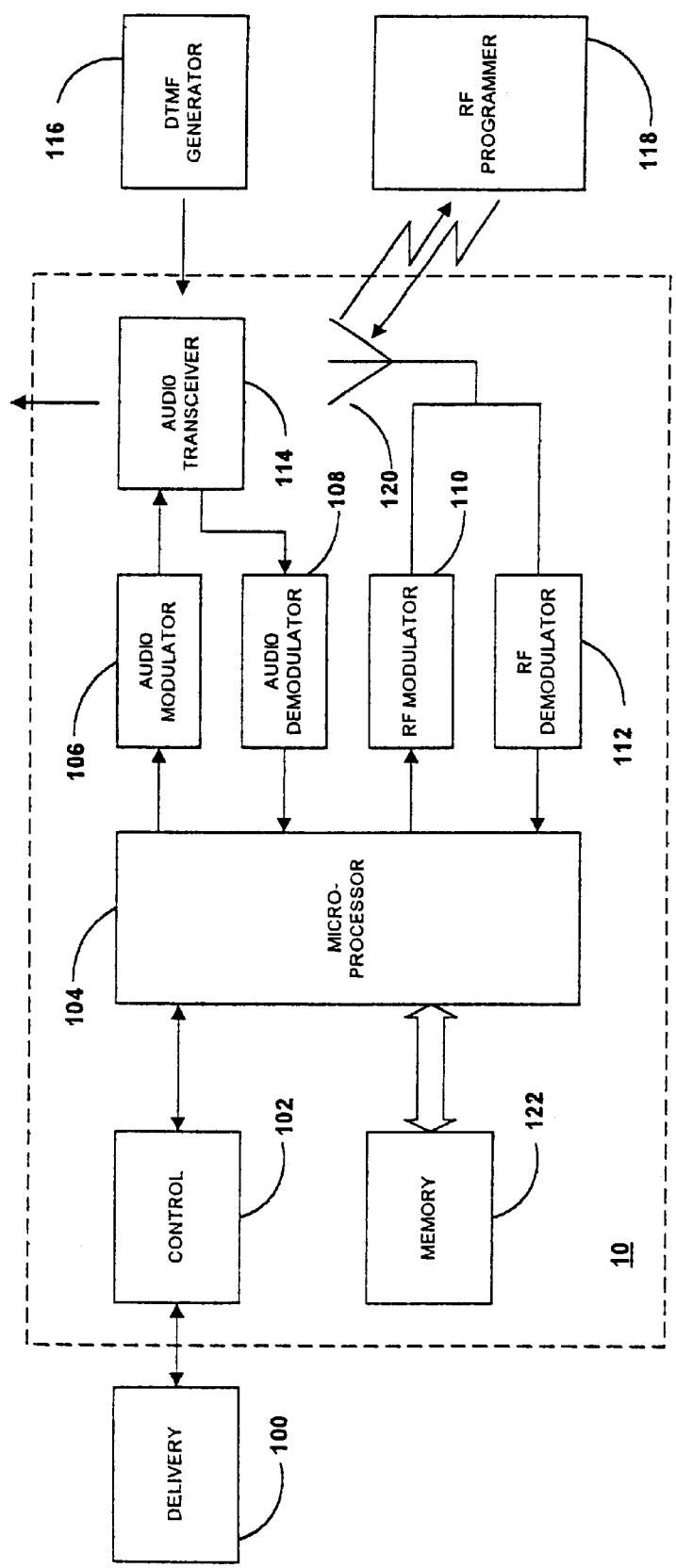
FIG. 1 is a functional block diagram of an IMD and EMD according to a first preferred embodiment of the present invention.

FIG. 1 illustrates a first embodiment of the invention. The IMD 10 includes a control mechanism 102 for controlling one or more operations of the IMD, which may include provision of one, or more desired therapies and/or monitoring one or more physiologic parameters within the patient, coupled to a mechanism 100 for delivering the desired therapies and/or sensing the physiologic parameters to be monitored. In the context of IMDs as discussed above, the controlling mechanism 102 might be a cardiac pacemaker or defibrillator, for example, capable of generating cardiac pacing and/or pulses and responding to depolarizations of one or more chambers of a patient's heart. In this example, the delivery mechanism 100 might be one or more electrodes, capable of stimulation heart tissue and receiving electrical signals indicative of heart depolarizations and optionally may include one or more additional physiologic sensors. Alternatively, control mechanism 102 might be a drug pump, with delivery mechanism 100 taking the form of a delivery catheter and optionally may include one or more additional physiologic sensors. Corresponding alternative configurations of the IMD might include corresponding control and delivery apparatus appropriate to implantable monitors, nerve stimulators or the like, as is typical of such IMDs.

The control mechanism 102 preferably operates under control of a microprocessor 104, which provides supervisory control of all components of the IMD 10. The IMD 10 further preferably includes a memory 122 that stores information relative to operational parameters of the IMD and relative to physiologic parameters sensed by the IMD, collectively referred to herein as patient data. The contents of memory 122 include information to be telemetered to an associated external programmer/monitor 118 and information received from the associated external programmer/monitor 118 indicative of the desired operational mode of the IMD 10.

The IMD 10 includes an antenna 120 coupled to RF modulation circuitry 110 and RF demodulation circuitry 112 for transmitting information to and receiving information from external programmer/monitor 118. It will be understood that the external programmer/monitor or EMD 118 also comprises an antenna and RF modulation and demodulation circuitry. External programmer/monitor or EMD 118 communicates with the IMD 10 in the illustrated embodiment by means of an RF link, as is conventional in the context of IMD programmers. The antenna 120 and associated modulation and demodulation circuitry 110 and 112 and the external programmer/monitor 118 may correspond to any of those described in the patents discussed above. However, the invention is believed particularly beneficial in the context of IMDs which are adapted to communicate with programmers/monitors located remote from the patient as described in the Villaseca et al. and Goedeke patent applications and the Nappholz patent discussed above.

The IMD 10 is also provided with an audio transceiver 114 which may take the form of a microphone/speaker, for example, a piezo-electric transducer, which is coupled to associated audio modulation and demodulation circuitry 106 and 108. Modulation and demodulation circuitry 106 and 108 may correspond to any known circuitry employed to create and decode DTMF tones as employed by touch-tone telephony. For example, demodulation circuitry 108 may correspond to commercially available DTMF decoder chips as manufactured by Motorola, Inc. and others and modulation circuitry 106 may correspond to DTMF tone generator circuits as employed in modern touch-tone telephones. Modulation circuitry may alternatively or in addition generate audio signals other than DTMF tones. DTMF tone sequence generator 116 may be a IMD such as an auto-dialer, having the capability of generating desired sequences of DTMF tones, preferably in response to the push of a single button. The audio transceiver 114 and the associated audio modulation and demodulation circuitry 106 and 108 can be incorporated into a relatively small space of the IMD 10 at low cost. This change in IMD circuitry and architecture eliminates the need for the conventional, relatively bulky and expensive, magnetic reed switch that takes up valuable physical space within the IMD 10 and adds to its manufacturing cost.

The DTMF tone generator 116 may be employed, for example, as part of a programming or follow-up procedure, in conjunction with a programmer/monitor 118 which does not need to be in close proximity to the patient. In such case, the patient may be seated at a distance of several feet from the programmer/monitor 118, the physician may activate the programmer/monitor 118 and the patient may employ the DTMF tone generator 116 to activate the RF telemetry of the IMD 10. The audio transceiver 114 may optionally be activated to generate a DTMF tone or is other tone or a series of DTMF tones or other tones indicating either successful activation of the IMD's telemetry or successful establishment of reliable communication between the IMD 10 and programmer/monitor 118. In some embodiments of the invention, the audio transceiver 114 may additionally be employed to provide tones indicative of other aspects of the operation or status of the IMD 10, which tones may also be received and demodulated by an audio receiver in the EMD associated with the IMD 10.

The DTMF tone generator 116 may also be employed to change the operational mode of the IMD 10. For example, if IMD 10 is a cardiac pacemaker, DTMF tone generator 116 may be employed to cause the IMD 10 to operate in an asynchronous mode to allow the patient or physician to determine the pacemaker's present rate by taking the patient's pulse rate. Similarly, the DTMF generator may be employed in conjunction with electrogram monitoring equipment, either in the physician's office or trans-telephonic, in order to facilitate recording of a paced electrogram.

The preceding discussion of the use of the DTMF tone generator 116 describes its use as stand-alone EMD that can be used alone or cooperatively with the programmer/monitor or EMD 118. However, it should also be understood that in cases in which a programmer or monitor is provided which employs a programming head intended for use closely adjacent the IMD, a DTMF tone generator 116 will of course also be included in the programming head in substitution for the conventional permanent magnet.

Recently, it has become common to provide the patient with a limited function programmer/monitor 118, particularly in conjunction with implanted neurostimulators and implanted atrial defibrillators. In the context of implanted neurostimulators, the patient's programmer/monitor 118 typically provides the patient with the ability to adjust the amplitude of the neurostimulation pulses and to disable the IMD 10. In the context of implanted atrial defibrillators, the patient's programmer/monitor 118 typically provides the patient with the ability to trigger or override the deliver of atrial defibrillation pulses. In conjunction with these types of IMDs, a DTMF tone generator 116 may be employed with such a patient programmer/monitor 118 or incorporated within such a patient programmer/monitor 118 to enable telemetry transmission from the IMD 10.

As an added benefit, in some embodiments of the invention, particularly in cases where it is desirable that the patient has a limited capability to program the IMD 10, the DTMF tone generator 116 may serve as an alternate mechanism for permanently modifying the operational parameters of the IMD 10 or triggering therapy delivery. For example, in the case in which the DTMF tone generator 116 takes the form of an auto-dialer, and the IMD 10 takes the form of an implanted pacemaker/atrial defibrillator, the DTMF generator 116 may store tone sequences which will activate the IMD's telemetry system, switch the operation of the pacemaker portion of the IMD to asynchronous mode, reduce the pacing rate at night to assist sleep and/or disable, override or trigger atrial defibrillation therapies, eliminating the necessity of a more expensive RF type patient programmer/monitor 115 entirely. In this case, if the DTMF tone generator 118 provided by the physician is lost or broken, it may also be readily replaced at little cost to the patient. In a pinch, the patient may even employ his or her touch-tone phone to manually generate the DTMF tone sequences to affect the desired operational changes, preferably while in telephone communication with the physician.

The EMD employed to deliver the DTMF tone sequence may be similar to an auto-dialer, of the type available at electronics stores, pre-programmed with one or more sequences of tones. Alternatively, or if the physician provided EMD is lost or broken, an off the shelf auto-dialer may be employed, with one or more memorized numbers used to activate the IMD telemetry or to trigger a change in operating mode. Alternatively, the patient's own touch-tone phone preferably a phone with the capability to memorize several phone numbers might be employed.

Because the DTMF tone-generating IMD (e.g. an auto-dialer) can store multiple sequences of tones, it may be employed to control multiple operational parameters and/or activate IMD telemetry independently of mode changes, a benefit not typically available using a simple magnet. As an added benefit, the DTMF tone generating IMD may also have the patient's physician's phone number memorized and may also be used to assist in contacting the physician.

In preferred embodiments of the invention, the IMD also includes a mechanism for generating audible feedback to indicate to the patient and/or physician that the DTMF tones have been received. For example, the microphone within the IMD may also serve as a speaker and may be driven by associated audio modulation circuitry within the IMD. The audio feedback may include differing series of tones, depending on the information to be conveyed.

The use of the DTMF tone generator 116 either as a stand-alone EMD or incorporated into typical programmer/monitor 118 eliminates the heavy, bulky, and relatively expensive magnet, and also eliminates the relatively bulky magnetic reed switch incorporated into the IMD 10 while only minimally affecting the size and expense of the associated circuitry. This change makes it possible to provide a patient programmer or EMD that is relatively small and inexpensive and enables the incorporation of other features that can be advantageously employed by the patient.

Figure 2:
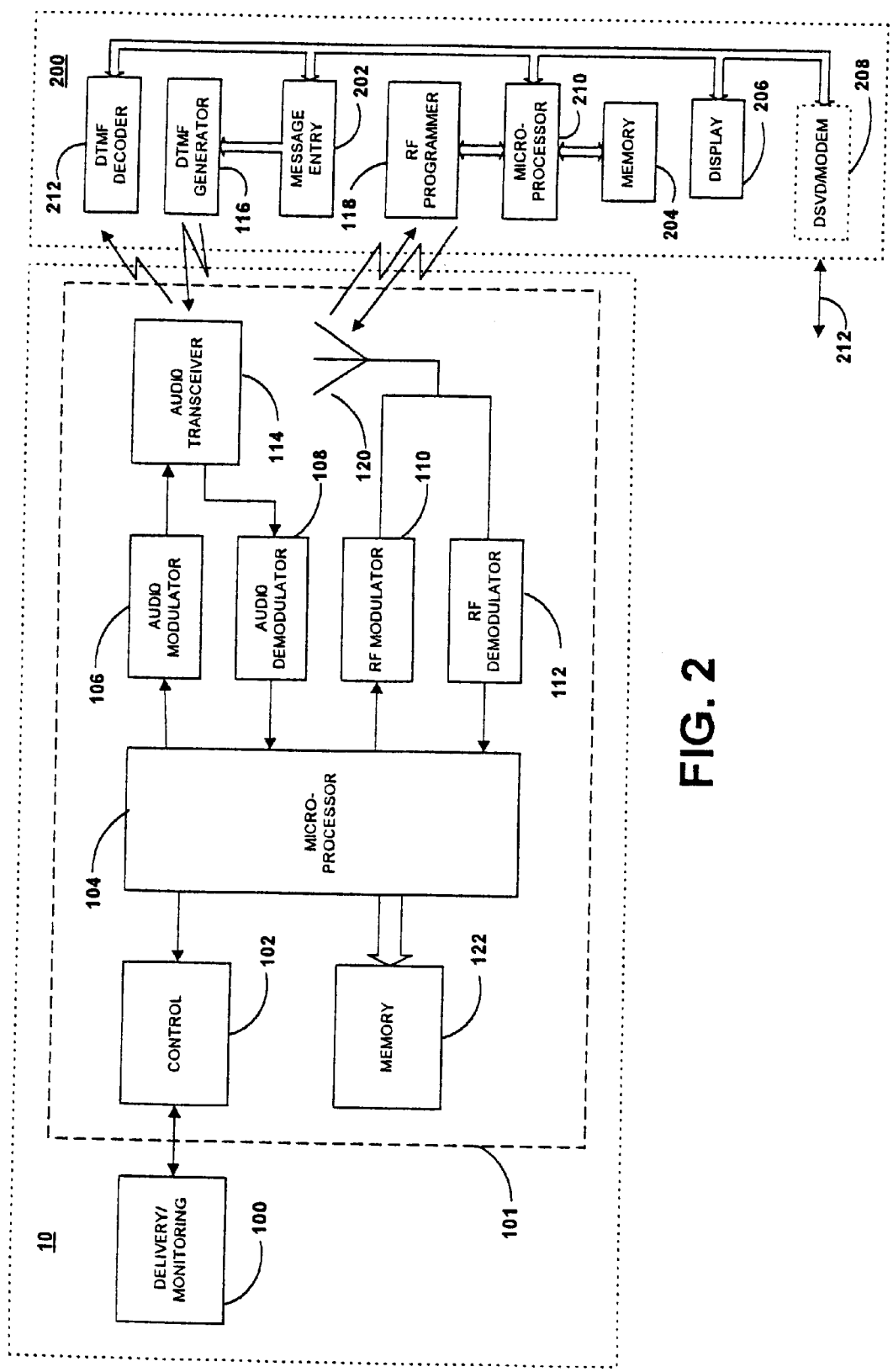
FIG. 2 is a functional block diagram of an IMD and EMD according to a second preferred embodiment of the present invention.

FIG. 2 illustrates a further embodiment of the invention, wherein the DTMF tone generator 116 and the RF programmer 118 are incorporated into such a patient programmer or EMD 200 having a number of further features that can be employed in combination to enhance bi-directional communications. The EMD 200 preferably is miniaturized and battery powered. The functions of EMD 200 are preferably controlled by hardware or firmware including one or more digital signal processor (DSP) associated with a microprocessor and employing software resident in memory. Certain features of a hand-held personal digital assistant (PDA) can be advantageously employed in EMD 200 to provide human understandable communications between the EMD and IMD in the form of exchanged messages.

The EMD 200 therefore preferably comprises a microprocessor 210, coupled through control lines and data buses with the above-described DTMF generator 116 and RF programmer 118 incorporated into a single housing. The EMD 200 also includes a message entry mechanism 202 for entering messages (e.g., a miniaturized keyboard or a sensitive screen), RAM and ROM memory 204, and a display 206 (e.g., an LCD screen) for displaying the user entered messages and the response messages from the IMD.

Figure 3:
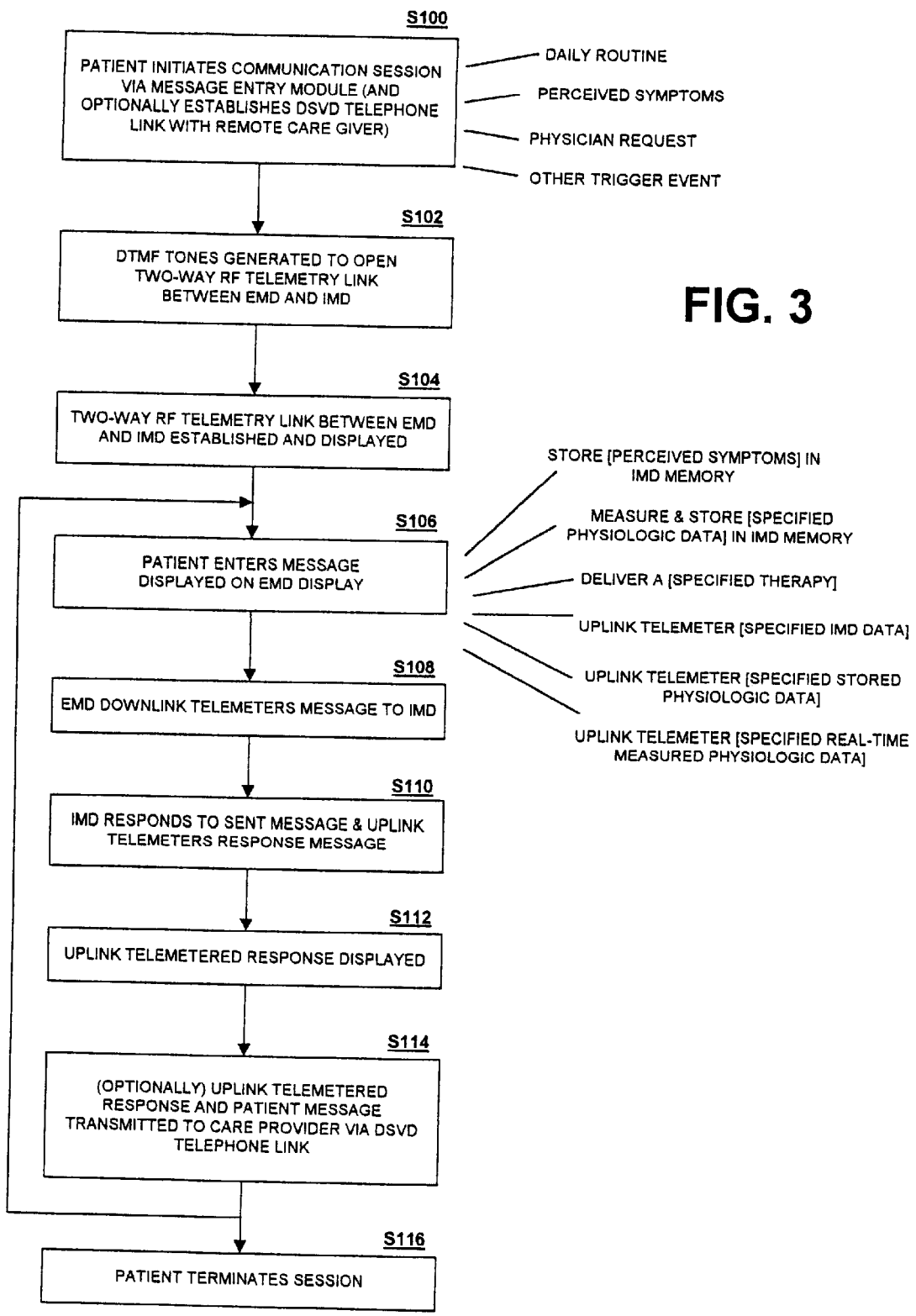
FIG. 3 is a flow chart illustrating the uses of the IMD and EMD of FIG. 2 in accordance with the present invention.

In uses depicted in FIG. 3, a communication link is established in the manner described above between the EMD 200 and the IMD 10 when the IMD 10 detects encoded DTMF tones emitted by the DTMF generator 116. In this embodiment, the patient or other user enters a command via message entry mechanism 202 to wake the IMD 10 to enable uplink and downlink telemetry transmissions in a telemetry or communication session. Then, the patient or other user of the EMD 200 formulates a message that communicates an instruction or query to the IMD 10 using the message entry mechanism 202. The message is optionally displayed by display 206 as it is composed by the user and is then downlink telemetered to the IMD 10 via the RF programmer 118. A response message from the IMD 10 is uplink telemetered, received by RF programmer 118, stored in RAM in memory 204 and displayed by display 206.

The EMD 200 optionally includes a DSVD/modem module 206 for either connection to a telephone line or a cellular telephone receiver in a variety of ways that can provide two-way voice communication between the patient and a remote care provider as well as transmission of uplink telemetered IMD and patient data to a remote EMD. The DSVD (digital simultaneous voice and data) transmissions can be effected constitute a common public switched telephone (PSTN) line as described, for example, in U.S. Pat. No. 5,941,829, issued to Salzstein et al., or other communication modes described in commonly assigned U.S. Pat. No. 5,752,976, issued to Duffin et al. and U.S. Pat. No. 6,083,248, issued to Thompson.

FIG. 3 illustrates how the EMD 200 of this embodiment of the present invention can be used by a patient or a health care provider on site with the patient in a typical telemetry or communication session in order to change IMD function, interrogate IMD and patient data, or to effect storage of information in the IMD memory 122. In step S100, the patient (or bedside care provider) initiates the communication session using the message entry module 202.

The initiation and content of the session can be prescribed by the health care provider, e.g., to measure physiologic parameters and provide the real-time patient data or an indication that the parameters are acceptable or not to the patient. For example, the patient may be advised to check blood pressure at a particular time, and the IMD 10 or the EMD 100 can be programmed to advise the patient that the blood pressure is acceptable or is not acceptable and to take a prescribed medication or contact the remote care provider. This instruction can be a standing instruction to initiate and complete the session on a daily basis at a particular time of day.

Or the patient can be instructed by a telephone call from the patient's primary health care provider to commence the communication session. The DSVD/modem telephone link with the remote health care provider can be employed in this case to transmit the uplink telemetered patient data to the health care provider. In addition, the remote health care provider can transmit programming commands through the DSVD/modem into EMD memory 204 for downlink telemetry transmission in step S108 (bypassing step S106) to the IMD 10 to re-program an operating mode or parameter value.

Or, the patient may experience symptoms that are associated with the monitoring or therapy delivery function of the IMD 10 and can wake up the IMD 10 to deliver a therapy and/or to store physiologic data with a date and time stamp associated with a message relating to the symptoms composed and downlink telemetered by the patient. For example, a patient can experience pain, heart palpitations, or the like, and perform the steps of FIG. 3 to chronicle the episode along with data associated with a delivered therapy and/or related physiologic data. The user can compose a message about the symptoms using the message entry module 202 and trigger downlink telemetry of the message to the IMD 10 for storage in memory 122.

A single designated EMD push-button can be depressed or a display screen site can be contacted to initiate the generation of the DTMF tones by generator 116 in step S102, thereby enabling commencement of a communication session with the IMD 10. In step S104 of this embodiment, a two-way RF telemetry link is established between the RF transceivers of the IMD 10 and the EMD 200 as described above, and the status of the link is displayed on the display 206.

Then in step S106, the patient enters a downlink message through the message entry mechanism 202 of the EMD 200 to be communicated to the IMD 10 via a downlink telemetry transmission, and that message is displayed on display 206. The communication and its contents can be prompted by a number of events, as described above with respect to step S100. Exemplary messages are shown in FIG. 3. The formatting of a recognizable message can be effected by interactive software resident in EMD 200 that prompts the patient to insert specific instructions within a given message format. Or symbols can be displayed on the display that the patient can select alone or in combinations to form a displayed message.

The displayed message is then edited by the patient in step S106. When editing is finished, the patient enters a transmit command via the message entry mechanism 202 causing the message to be encoded and downlink telemetry transmitted in step S108 to the IMD 10.

Alternatively, for certain messages, the message can be formulated into a train of DTMF tones that are emitted using the DTMF tone generator 116 as described above. For example, if the patient requires an immediate therapy, a simple "panic button" can be depressed or contacted that combines steps S100–S108 to generate a train of DTMF tones that wakes up the IMD 10 and commands delivery of the therapy.

In step S108, the IMD 10 receives and decodes the sent or downlink message, performs the requested action, and uplink telemeters an uplink or response message that is displayed on display 206. The displayed, uplink telemetered, response message either contains requested patient data and/or confirms the actions taken.

Or, the patient can be instructed by a displayed warning to take actions, e.g. to take a medication or contact emergency health care. The instruction to the patient would be based on an analysis of physiologic data measured by the IMD 10 in response to the sent message by algorithms processed by the microprocessor 104. However, the uplink telemetered message may simply be the physiologic data, and the analysis of the physiologic data can be conducted by algorithms processed by the microprocessor 210 of EMD 200, culminating in the displayed instruction.

Alternatively, certain response messages could be conveyed as a generated train of DTMF tones emitted by audio transceiver 114 and either heard by the patient or received by an optional DTMF decoder 212 and displayed on display 206 and/or stored in memory 204 Optionally, the patient composed message and the uplink telemetered response message can be forwarded in step S114 to the remote health care provider if an open telecommunication link 212 is enabled to the remote location via the DSVD/modem 208.

Steps S106–S114 can be repeated as many times as necessary, and the patient then terminates the session in step S116. The termination can be effected by a simple "QUIT" command entered in step S106 causing steps S108–S112 to be completed to close the telemetry link established in step S104. The session can also be terminated by time-out of a session timer.

Any patents or publications referenced herein are incorporated by reference in their entireties.

While the present invention has been illustrated and described with particularity in terms of a preferred embodiment, it should be understood that no limitation of the scope of the invention is intended thereby. The scope of the invention is defined only by the claims appended hereto. It should also be understood that variations of the particular embodiment described herein incorporating the principles of the present invention will occur to those of ordinary skill in the art and yet be within the scope of the appended claims.

What is claimed is:

1. A method of communicating between an external medical device (EMD), and an implantable medical device (IMD) including means for delivering a therapy to a patient or monitoring a physiologic parameter of a patient and control means for modifying operation of the IMD in response to control instructions received from the EMD, the method comprising the steps of:

generating encoded dual tone multiple frequency (DTMF) tones from the EMD to enable commencement of a communication session with the IMD;

detecting the encoded DTMF tones by the IMD; and establishing a communication link between the EMD and the IMD in response to detection of the encoded DTMF tones by the IMD.

2. The method of claim 1, further comprising the steps of:

communicating an uplink message from the IMD to the EMD; and displaying the uplink message on a display of the EMD.

3. The method of claim 1, further comprising the steps of:

using a message entry mechanism of the EMD, entering a downlink message to be communicated to the IMD;

communicating the downlink message from the EMD to the IMD;

communicating an uplink message from the IMD to the EMD; and displaying one or both of the uplink and downlink messages on a display of the EMD.

4. The method of claim 1, further comprising the steps of:

using a message entry mechanism of the EMD, entering a downlink message to be communicated to the IMD; and communicating the downlink message from the EMD to the IMD.

5. The method of claim 1, further comprising the steps of:

using a message entry mechanism of the EMD, entering a downlink message to be communicated to the IMD;

communicating the downlink message from the EMD to the IMD; and communicating an uplink message from the IMD to the EMD.

6. The method of claim 1, further comprising the steps of:

using a message entry mechanism of the EMD, entering a downlink message to be communicated to the IMD instructing the control means to provide a therapy; and communicating the downlink message from the EMD to the IMD.

7. The method of claim 1, further comprising the steps of:

using a message entry mechanism of the EMD, entering a downlink message to be communicated to the IMD instructing the control means to provide a therapy;

communicating the downlink message from the EMD to the IMD; and communicating an uplink message from the IMD to the EMD confirming delivery of the therapy.

8. The method of claim 1, further comprising the steps of:

using a message entry mechanism of the EMD, entering a downlink message to be communicated to the IMD instructing the control means to provide a therapy;

communicating the downlink message from the EMD to the IMD;

communicating an uplink message from the IMD to the EMD confirming delivery of the therapy; and displaying one or both of the uplink and downlink messages on a display of the EMD.

9. The method of claim 1, further comprising the steps of:

using a message entry mechanism of the EMD, entering a downlink message to be communicated to the IMD instructing the control means to uplink communicate patient data; and communicating the downlink message from the EMD to the IMD.

10. The method of claim 1, further comprising the steps of:

using a message entry mechanism of the EMD, entering a downlink message to be communicated to the IMD instructing the control means to uplink communicate patient data;

communicating the downlink message from the EMD to the IMD; and communicating an uplink message from the IMD to the EMD related to the measured physiologic condition.

11. The method of claim 1, further comprising the steps of:

using a message entry mechanism of the EMD, entering a downlink message to be communicated to the IMD instructing the control means to uplink communicate patient data;

communicating the downlink message from the EMD to the IMD;

communicating an uplink message from the IMD to the EMD related to the measured physiologic condition; and displaying one or both of the uplink and downlink messages on a display of the EMD.

12. The method of claim 1, further comprising the steps of:

using a message entry mechanism of the EMD, entering a downlink message to be communicated to the IMD instructing the control means to measure a physiologic condition of the patient; and communicating the downlink message from the EMD to the IMD.

13. The method of claim 1, further comprising the steps of:

using a message entry mechanism of the EMD, entering a downlink message to be communicated to the IMD instructing the control means to measure a physiologic condition of the patient;

communicating the downlink message from the EMD to the IMD; and communicating an uplink message from the IMD to the EMD related to the measured physiologic condition.

14. The method of claim 1, further comprising the steps of:

using a message entry mechanism of the EMD, entering a downlink message to be communicated to the IMD instructing the control means to measure a physiologic condition of the patient;

communicating the downlink message from the EMD to the IMD;

communicating an uplink message from the IMD to the EMD related to the measured physiologic condition; and displaying one or both of the uplink and downlink messages on a display of the EMD.

15. The method of claim 1, further comprising the steps of:

using a message entry mechanism of the EMD, entering a downlink message to be communicated to the IMD instructing the control means to store the message for later uplink message transmission; and communicating the downlink message from the EMD to the IMD.

16. The method of claim 1, further comprising the steps of:

using a message entry mechanism of the EMD, entering a downlink message to be communicated to the IMD instructing the control means to store the message for later uplink message transmission and instructing the control mechanism to measure a physiologic condition of the patient;

communicating the downlink message from the EMD to the IMD; and communicating an uplink message from the IMD to the EMD related to the measured physiologic condition.

17. The method of claim 1, further comprising the steps of:

using a message entry mechanism of the EMD, entering a downlink message to be communicated to the IMD instructing the control means to store the message and instructing the control mechanism to measure and store a physiologic condition of the patient for later uplink message transmission;

communicating the downlink message from the EMD to the IMD;

communicating an uplink message from the IMD to the EMD related to the measured physiologic condition; and displaying one or both of the uplink and downlink messages on a display of the EMD.

18. A method of communicating between an external medical device (EMD), and an implantable medical device (IMD) including means for delivering a therapy to a patient or monitoring a physiologic parameter of a patient and control means for modifying operation of the IMD in response to control instructions received from the EMD, the method comprising the steps of:

generating encoded dual tone multiple frequency (DTMF) tones from the EMD to enable commencement of a communication session with the IMD;

detecting the encoded DTMF tones by the IMD;

establishing a two-way communication link between the EMD and the IMD in response to detection of the encoded DTMF tones by the IMD;

using a message entry mechanism of the EMD, entering a downlink message to be communicated to the IMD;

communicating the downlink message from the EMD to the IMD;

communicating an uplink message from the IMD to the EMD; and displaying one or both of the uplink and downlink messages on a display of the EMD.

19. The method of claim 18, wherein the step of entering a downlink message further comprises entering a downlink message to be communicated to the IMD instructing the control means to provide a therapy.

20. The method of claim 18, wherein the step of entering a downlink message further comprises entering a downlink message to be communicated to the IMD instructing the control means to communicate an uplink message comprising specified patient data.

21. The method of claim 18, wherein the step of entering a downlink message further comprises entering a downlink message to be communicated to the IMD instructing the control means to measure a physiologic condition of the patient.

22. The method of claim 18, wherein the step of entering a downlink message further comprises entering a downlink message to be communicated to the IMD instructing the means to store the message and instructing the control mechanism to measure and store a physiologic condition of the patient for later uplink message transmission.

23. The method of claim 18, wherein the step of entering a downlink message further comprises entering a downlink message to be communicated to the IMD instructing the control means to store the downlink message for later uplink message transmission.

24. A system for communicating between an implantable medical device (IMD) implanted in a patient and an external medical device (EMD) having a display comprising:

in the EMD, means for generating encoded dual tone multiple frequency (DTMF) tones from the EMD to enable commencement of a communication session with the IMD; and in the IMD, delivery means for delivering a therapy to the patient or monitoring a physiologic condition of the patient;

control means for modifying operation of the IMD in response to a downlink message received from the EMD;

means for detecting the encoded DTMF tones generated by the EMD and for establishing a communication link between the EMD and the IMD; and uplink message means for communicating an uplink message from the IMD to the EMD.

25. The system of claim 24, further comprising, in the EMD, means for receiving and displaying the uplink message on the display of the EMD.

26. A system for communicating between an implantable medical device (IMD) implanted in a patient and an external medical device (EMD) having a display comprising:

in the EMD, means for generating encoded dual tone multiple frequency (DTMF) tones from the EMD to enable commencement of a communication session with the IMD;

message entry means for entering a downlink message to be communicated to the IMD; and means for communicating the downlink message from the EMD to the IMD; and in the IMD, means for detecting the encoded DTMF tones generated by the EMD and for establishing a communication link between the EMD and the IMD;

delivery means for delivering a therapy to a patient or monitoring a physiologic parameter of a patient; and control means for modifying an operation of the IMD in response to a downlink message received from the EMD.

27. The system of claim 26, further comprising, in the EMD, means for displaying the downlink messages on the display of the EMD.

28. The system of claim 27, wherein the message entry means further comprises means for entering a downlink message to be communicated to the IMD instructing the control means to provide a therapy.

29. The system of claim 27, wherein the message entry means further comprises means for entering a downlink message to be communicated to the IMD instructing the control means to communicate an uplink message comprising patient data.

30. The system of claim 27, wherein the message entry means further comprises means for entering a downlink message to be communicated to the IMD instructing the control means to measure a physiologic condition of the patient.

31. The system of claim 27, wherein the message entry means further comprises means for entering a downlink message to be communicated to the IMD instructing the control means to store the message and instructing the control mechanism to measure and store a physiologic condition of the patient for later uplink message transmission.

32. The system of claim 27, wherein the message entry means further comprises means for entering a downlink message to be communicated to the IMD instructing the control means to store the downlink message for later uplink message transmission.

33. The system of claim 26, wherein the message entry means further comprises means for entering a downlink message to be communicated to the IMD instructing the control means to provide a therapy.

34. The system of claim 26, wherein the message entry means further comprises means for entering a downlink message to be communicated to the IMD instructing the control means to communicate and uplink message comprising patient data.

35. The system of claim 26, wherein the message entry means further comprises means for entering a downlink message to be communicated to the IMD instructing the control means to measure a physiologic condition of the patient.

36. The system of claim 26, wherein the message entry means further comprises means for entering a downlink message to be communicated to the IMD instructing the control means to store the message and instructing the control mechanism to measure and store a physiologic condition of the patient for later uplink message transmission.

37. The system of claim 26, wherein the message entry means further comprises means for entering a downlink message to be communicated to the IMD instructing the control means to store the message for later uplink message transmission.

38. A system for communicating uplink and downlink messages between an implantable medical device (IMD) implanted in a patient and an external medical device (EMD) having a display comprising:

in the EMD, means for generating encoded dual tone multiple frequency (DTMF) tones from the EMD to enable commencement of a communication session with the IMD;

message entry means for entering a downlink message to be communicated to the IMD;

means for communicating the downlink message from the EMD to the IMD; and means for displaying one or both of the uplink and downlink messages on the display of the EMD; and in the IMD, delivery means for delivering a therapy to a patient or monitoring a physiologic parameter of a patient;

control means for modifying operation of the IMD in response to a downlink message received from the EMD;

means for detecting the encoded DTMF tones generated by the EMD and for establishing a communication link between the EMD and the IMD; and uplink message means for communicating an uplink message from the IMD to the EMD.

39. The system of claim 38, wherein the message entry means further comprises means for entering a downlink message to be communicated to the IMD instructing the control means to provide a therapy.

40. The system of claim 38, wherein the message entry means further comprises means for entering a downlink message to be communicated to the IMD instructing the control means to communicate an uplink message comprising patient data.

41. The system of claim 38, wherein the message entry means further comprises means for entering a downlink message to be communicated to the lMD instructing the control means to measure a physiologic condition of the patient.

42. The system of claim 38, wherein the message entry means further comprises means for entering a downlink message to be communicated to the IMD instructing the control means to store the message and instructing the control mechanism to measure and store a physiologic condition of the patient for later uplink message transmission.

43. The system of claim 38, wherein the message entry means further comprises means for entering a downlink message to be communicated to the IMD instructing the control means to store the message for later uplink message transmission.

44. A method of communicating between an external medical device (EMD), and an implantable medical device (IMD) including means for delivering a therapy to a patient or monitoring a physiologic parameter of a patient and control means for modifying operation of the IMD in response to control instructions received from the EMD, the method comprising the steps of:

generating encoded dual tone multiple frequency (DTMF) tones from the EMD;

detecting the encoded DTMF tones by the IMD; and modifying the operation of the IMD responsive to received DTMF tone sequences, wherein the IMD and EMD further include a telemetry system and wherein modifying the operation of the IMD comprises modifying operation of the telemetry system responsive to received DTMF tone sequences.

45. The method of claim 44, wherein modifying the operation of the IMD comprises modifying operation of the means for delivering a therapy to a patient or monitoring a physiologic parameter responsive to received DTMF tone sequences.

46. The method of claim 44, wherein the IMD comprises an audio tone generator, and further comprising generating an audio tone or series of tones indicative of operation or status of the IMD.

47. The method of claim 44, wherein the IMD and EMD further include a telemetry system and wherein modifying the operation of the IMD comprises establishing a communication link between the EMD and the IMD in response to detection of the encoded DTMF tones by the IMD.

48. A system for communicating between an external medical device (EMD), and an implantable medical device (IMD) including means for delivering a therapy to a patient or monitoring a physiologic parameter of a patient and control means for modifying operation of the IMD in response to control instructions received from the EMD, the system comprising:

means for generating encoded dual tone multiple frequency (DTMF) tones from the EMD;

means for detecting the encoded DTMF tones by the IMD; and means for modifying the operation of the IMD responsive to received DTMF tone sequences, wherein the IMD and EMD further include a telemetry system and wherein the means for modifying the operation of the IMD comprises means for modifying operation of the telemetry system responsive to received DTMF tone sequences.

49. The system of claim 48, wherein the means for modifying the operation of the IMD comprises means for modifying operation of the means for delivering a therapy to a patient or monitoring a physiologic parameter responsive to received DTMF tone sequences.

50. The system of claim 48, wherein the IMD comprises an audio tone generator for generating an audio tone or series of tones indicative of operation or status of the IMD.

51. The system of claim 48, wherein the IMD and EMD further include a telemetry system and wherein the means for modifying the operation of the IMD comprises means for establishing a communication link between the EMD and the IMD in response to detection of the encoded DTMF tones by the IMD.

* * * * *